United States Patent [19]

Kajinami et al.

[11] 4,192,897

[45] Mar. 11, 1980

[54] HEAT TREATMENT FOR SINGLE-CELL MATERIALS AND RESULTANT PRODUCTS

[75] Inventors: Shingo Kajinami, Naperville; Elmer J. Saunders, Downers Grove; Philip G. Schnell, Wheaton, all of Ill.

[73] Assignee: Standard Oil Company (Indiana), Chicago, Ill.

[21] Appl. No.: 792,321

[22] Filed: Apr. 29, 1977

Related U.S. Application Data

[63] Continuation-in-part of Ser. No. 725,021, Sep. 20, 1976, abandoned.

[51] Int. Cl.² .......................... C12B 1/00; A23J 1/18
[52] U.S. Cl. ........................................ 426/60; 426/62; 426/656; 426/520

[58] Field of Search .................. 426/456, 61, 62, 656, 426/60, 657, 520; 195/49, 82, 28 R; 260/112 R

[56] References Cited

U.S. PATENT DOCUMENTS

| | | | |
|---|---|---|---|
| 3,163,638 | 12/1964 | Miwa et al. | 195/82 X |
| 3,885,050 | 5/1975 | Ridgway et al. | 426/456 X |
| 3,991,215 | 11/1976 | Robbins | 426/60 |

*Primary Examiner*—R. B. Penland
*Attorney, Agent, or Firm*—Gregory E. Croft; Arthur G. Gilkes; William T. McClain

[57] ABSTRACT

Whole single-cell protein cells possessing improved functional properties are obtained by heat treating said cells at a temperature of from about 215° to about 300° F. for from about 30 seconds to about 25 minutes to inactivate invertase.

26 Claims, No Drawings

HEAT TREATMENT FOR SINGLE-CELL MATERIALS AND RESULTANT PRODUCTS

This application is a continuation-in-part of Ser. No. 725,021, filed Sept. 20, 1976 now abandoned.

BACKGROUND OF THE INVENTION

1. Field of the Invention

This invention relates to processes for treating single-cell materials to yield a product having improved functional properties. More particularly, it relates to a heat treatment of an aqueous yeast slurry in which the yeast is held at a particular temperature for a predetermined period of time. The optimal time-temperature relationship happens to coincide with a segment of the invertase deactivation curve, which makes invertase a convenient indicator for the completion of the heat treatment.

2. Description of the Prior Art

In recent years, a number of different proteinaceous materials have been developed for use as substitutes for the more traditional sources of protein in the human diet. Included among these proteinaceous materials are the single-cell micro-organisms such as fungi, bacteria, and yeasts. They are generally used in small amounts in a variety of food applications, depending upon their individual properties.

For example, spray-dried *Candida utilis* is a highly nutritious food product which is high in protein, B vitamins, and essential minerals. It is commercially produced by a fermentation process wherein pure ethyl alcohol, nutrients, and water are sterilized and metered into an aseptic fermentation vessel. Active *Candida utilis* yeast is then added and grown continuously while the fermentor contents, or broth, is continuously withdrawn. The broth is centrifuged to concentrate the yeast cells into a cream having a yeast cell concentration of about 10–20 weight percent. The cream is then pasteurized and spray-dried to a powder form. The resulting powdered yeast is an effective food supplement by itself or when used in combination with other protein sources. Because of the high food value of such a product, there has been continual interest in improving or varying its functional properties in order to make it more acceptable in various food applications.

It has now been discovered that by subjecting single-cell materials to a controlled heat treatment having temperatures of from about 215° to about 300° F., some of the functional properties of the product are improved. In particular, the heat-treated product exhibits improved acid bite suppression which is of particular importance in salad dressings. It also heightens sour cream flavor and increases smooth mouthfeel. In addition, the heat treated product exhibits other functional properties such as fat sparing, fat binding, emulsification and stabilization control, and water binding, and also benefits a variety of food products such as taco seasoning mix, stroganoff sauce, pizza sauce, and others by heightening flavors and reducing ingredients costs.

SUMMARY OF THE INVENTION

In one aspect, the invention resides in a process for imparting improved functional properties to whole cell single-cell protein materials comprising heating an aqueous slurry of the single-cell materials to a temperature of from about 215° to 300° F. for from about 30 seconds to about 25 minutes. A more preferred temperature range would be from about 255° to about 300° F. A still more preferred temperature range would be from about 260° to about 270° F.

In another aspect, the invention resides in a process for imparting improved functional properties to whole cell single-cell protein materials, the improvement comprising heating an aqueous slurry of single-cell materials at a temperature of from about 215° to about 300° F., and preferably from about 255° to about 275° F. for a period of time about sufficient to deactivate invertase. Invertase, which is an enzyme generally present in most single-cell materials in significant amounts, can be deactivated by subjecting it to various time-temperature conditions. Deactivation times and temperatures are inversely related, i.e. at higher temperatures only a relatively short duration is necessary to deactivate the invertase. At lower temperatures, however, a much longer time is necessary. Coincidentally, those conditions which are most effective in producing the desired results of this invention fall along, or at least very close to, a segment of the invertase deactivation curve (see Example 3). In particular, the times necessary to deactivate invertase when subjected to temperatures between 215° and 300° F., and preferably between 255° and 275° F., are about the same as those necessary to achieve the optimal desired improvements in product properties. Therefore, invertase activity can be used as a convenient indicator as to whether or not a particular heat treatment is optimal. It must be pointed out that some improvement in functional properties can still be obtained when the single-cell material is either undertreated or overtreated, but optimum conditions appear to lie along the deactivation curve.

More particularly, the invention resides in the above-said process wherein the single-cell protein material is a yeast. The yeast can be active or inactive. Preferred yeasts include *Candida utilis, Saccharomyces cerevisiae, Saccharomyces fragilis,* and *Saccharomyces carlsbergensis.*

In a further aspect, the invention resides in an improved process for producing a food-quality yeast wherein a yeast broth is continuously withdrawn from a fermentation zone, said yeast broth being subsequently concentrated into a cream which is in turn spray-dried to a powder form, the improvement comprising heating the yeast cream to a temperature of from about 255° to about 275° F. for a period of time long enough to deactivate invertase. The yeast broth generally has a cell concentration between 1 and 5 weight percent (dry basis), whereas the yeast cream will generally have a cell concentration from between 5 and 25 weight percent (dry basis). The preferred temperature for the heat treatment is about 265° F. and the preferred time of treatment is about 2–2.5 minutes.

In a further aspect, the invention resides in an improved process for the continuous production of food quality yeasts by aerobic growth of said yeasts in a fermentation zone on an aqueous ethanolic substrate in the presence of ammonia, an oxygen-containing gas, and an excess of essential nutrients, wherein said yeasts are withdrawn from said fermentation zone as a broth, concentrated to a cream by centrifugation, and spray-dried to powder form, the improvement comprising heating the yeast cream to a temperature of from about 260° to about 270° F. for a length of time of from about 2 to about 2.5 minutes. The preferred yeast is *Candida utilis* and the preferred temperature is about 265° F.

In all aspects of this invention, the heat treatment insures full pasteurization.

DESCRIPTION OF SPECIFIC EMBODIMENTS

The following examples will illustrate some of the features of this invention.

EXAMPLES 1 and 2: Detection of Invertase Activity

Invertase activity is essentially measured by reacting the invertase-containing sample with a sucrose solution and then colorimetrically analyzing for the invert sugar product.

For example, four 100 ml. samples of cream (15 weight percent live cell suspension) were separately heated in beakers with a constant agitation for different time periods: 0 min., 15 min., 30 min., and 45 min. at 93° C. The cell suspensions were then centrifuged to remove cell debris. The clear supernatants were dialyzed to remove salts and then assayed for invertase activity. The assay solution contained 1 ml. of sucrose solution (400 mg. sucrose/ml.) and 0.1 ml. of enzyme solution (the supernatant). The sucrose solution was made by dissolving 40 mg. of sucrose in 100 ml. of 0.02 M phosphate buffer (pH 4.5). The reaction was initiated by addition of 0.1 ml. enzyme solution to the sucrose solution and was allowed to proceed at 55° C. for 2 min. The reaction was terminated by addition of 1.0 ml. of Nelson's alkaline copper reagent. The reaction mixture, in a test tube, then was placed in boiling water and heated for 20 min. The tube was cooled and 1.0 ml. of arsenomolybdate reagent was added to the solution for color development. The color intensity was measured at 540 millimicrons after dilution of the solution with 7 ml. of water.

The results are shown below:

| Sample | Time | Relative Invertase Activity |
| --- | --- | --- |
| 1. Live cell suspension | 0 | 1700 |
| 2. Live cell suspension | 15 min. | 150 |
| 3. Live cell suspension | 30 min. | 37 |
| 4. Live cell suspension | 45 min. | 0 |

The invertase of the live cell suspension was completely inactivated in 45 min. at 93° C.

As a comparison, invertase deactivation was measured for samples containing spray-dried inactive cells (10 weight percent slurry). The results, indicated below, show that the spray-dried cells can be deactivated in shorter times than the live cells.

| Sample | Time | Relative Invertase Activity |
| --- | --- | --- |
| 1. Spray dried cell suspension | 15 min. | 110 |
| 2. Spray dried cell suspension | 30 min. | 0 |

It is believed that the spray drying process physically releases some of the bound invertase within the cells, leaving mostly free invertase. The free invertase is more readily deactivated than the bound invertase and therefore the spray-dried cells can be deactivated in a shorter period of time.

EXAMPLE 3: Invertase Deactivation Curve For Live Cells

The following data represent heat treatment times at which the invertase in live yeast cells will be deactivated at the given temperatures. The numbers in parentheses indicate times which were insufficient to completely deactivate the invertase.

| Temperature (°F.) | Time (minutes) |
| --- | --- |
| 200 | 45 (30) |
| 230 | 9 |
| 240 | 5 (3) |
| 244 | 3.6 |
| 250 | 5.0 (2) |
| 260 | 1.9 |
| 270 | 1.6 |

A plot of these points gives a curved line which, for purposes of this application, is called the "invertase deactivation curve". (The actual invertase deactivation curve lies slightly below this plot, but the plotted curve sufficiently serves the purpose of teaching those skilled in the art the essence of this invention.) It should be noted that the invertase is deactivated at any point on or above the curve.

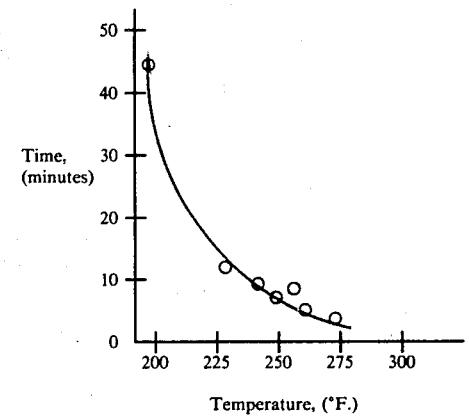

INVERTASE DEACTIVATION CURVE

EXAMPLES 4 and 5: Performance of Heat-Treated Live Yeast Cells in Yellow Cakes and Cookies To study the effects of heat treated single-cell protein materials, four samples of heat-treated *Candida utilis* yeast were incorporated into yellow cake and shortbread cookies as a replacement for 40% of the egg solids. Each sample was given a different time-temperature treatment. Samples 2 and 3 were treated at conditions closely corresponding to the invertase deactivation curve. The results are presented in TABLES I and II.

TABLE I

| | HEAT-TREATED YEAST AS A REPLACEMENT FOR 40% OF THE EGG SOLIDS IN YELLOW CAKE | | | | | | | | | |
| --- | --- | --- | --- | --- | --- | --- | --- | --- | --- | --- |
| Sample | Un-baked Weight (grams) | Baked Weight (grams) | Volume (cc.) | Flavor[1] | Texture[2] | External Color | Crumb Color[3] | Cell Structure[4] | Total Score[5] | Comments |
| Control | 450 | 393.00 | 1300 | 7 | 10 | golden | 10 | 22 | 87 | Yeasty |
| Sample #1 | 450 | 396.81 | 1325 | 10 | 6 | golden | 10 | 18 | 74 | Milk smell |

TABLE I-continued

HEAT-TREATED YEAST AS A REPLACEMENT FOR 40% OF THE EGG SOLIDS IN YELLOW CAKE

| Sample | Un-baked Weight (grams) | Baked Weight (grams) | Volume (cc.) | Flavor[1] | Texture[2] | External Color | Crumb Color[3] | Cell Structure[4] | Total Score[5] | Comments |
|---|---|---|---|---|---|---|---|---|---|---|
| 250° F./2 min. Sample #2 | 450 | 393.73 | 1350 | 10+ | 10 | golden | 10 | 28 | 94 | and taste |
| 260° F./2 min. Sample #3 | 450 | 396.81 | 1325 | 10+ | 10 | golden | 10 | 30 | 100 | Eggy and very sweet |
| 270° F./2 min. Sample #4 | 450 | 398.55 | 1400 | 10 | 6 | golden | 10 | 26 | 92 | Gummy texture |
| 255° F./5 min. | | | | | | | | | | |

[1]Evaluated by expert taste panel, with score of 10 being best and score of 0 the worst (foreign flavor).
[2]Evaluated by expert taste panel for overal texture in relation to moisture, tenderness, and softness. Score of 10 is best, 0 is worst.
[3]Evaluated by expert taste panel with 10 representing brightness and good yellow color and 0 representing dull and off color.
[4]Evaluated by expert taste panel with 30 representing good cell uniformity, size, and thickness and 0 representing poor in all respects.
[5]Approved method of American Association of Cereal Chemists, AACC Method 10-90.

TABLE II

HEAT-TREATED YEAST IN SHORTBREAD COOKIES

| Sample | Sample Description | % Soluble Solids | % Hydration | pH | Cookie Test[1] |
|---|---|---|---|---|---|
| Control | No heat treatment | 14.6 | 185 | 5.85 | 1.6 |
| Sample #1 | 250° 2 min. | 14.85 | 255.85 | 6.0 | 4.7 |
| Sample #2 | 260° 2 min. | 15.2 | 256.95 | 5.975 | 6.1 |
| Sample #3 | 270° 2 min. | 16.4 | 246.1 | 5.975 | 5.6 |
| Sample #4 | 255° 5 min. | 15.55 | 256.2 | 5.95 | 5.3 |

[1]Shortbread cookies with 1.85% test product were evaluated by expert taste panel for flavor and texture. Score of 10 is best, 0 is poorest.

As shown in TABLE I, flavor improvement in yellow cakes was obtained at all levels of heat treatment, although the best results were achieved with Samples 2 and 3, which were treated more closely to the condition of the invertase deactivation curve. Sample 1 was undertreated, whereas Sample 4 was overtreated. Nevertheless, there was an overall flavor improvement over the control by all four samples. This illustrates the fact that improved functional properties of single-cell protein materials, and particularly yeast, can be achieved through a heat treatment, with optimal results occurring when the heat treatment corresponds to the conditions on the invertase deactivation curve.

TABLE II illustrates that Samples 2 and 3 again have better performance, this time in shortbread cookies.

The following Examples 6–16 will serve to further illustrate the advantages of using a heat-treated single-cell protein material (heat-treated yeast) in various food formulations. In producing this product, a normal yeast cell cream (*Candida utilis*), having a yeast cell concentration of about 17 weight percent, is heated to about 265° F.±5° with an intermediate preheat of 110°–180° F. to aid in bringing the cream up to the desired temperature. The heated suspension is held at temperature for about 2.0–2.5 minutes and then spray-dried to a dry powder with less than about 6 weight percent moisture. The heat treatment is carried out in a continuous, plug flow manner. Although the residence time of the preheat step is not critical, the residence time at 265°±5° F. must be maintained between 2.0–2.5 minutes if an optimal product is to be produced.

A typical analysis of the heat-treated yeast used herein is as follows:

| Typical Composition, % | |
|---|---|
| Protein (N×6.25) | 52 |
| Fat* (acid hydrolysis) | 7 |
| Crude Fiber | 5 |
| Carbohydrates (by difference) | 22 |
| Moisture | 6 |
| Minerals | 8 |
| Phosphorus | 2 |
| Potassium | 2 |
| Magnesium | 0.3 |
| Calcium | 0.01 |
| pH | 6 |
| Total Sulfite | Less than 10 ppm (not detectable) |

| Microbiology | |
|---|---|
| Total plate count | Less than 1000/gm. |
| E. coli | negative |
| Salmonella | negative |
| Yeast/mold | 50/gm max. |

| Typical Amino Acid Analysis (g/16gN) | | | |
|---|---|---|---|
| Lysine | 6.7 | Alanine | 5.2 |
| Histidine | 1.8 | Cystine | 0.6 |
| Arginine | 6.6 | Valine | 5.0 |
| Aspartic | 8.4 | Methionine | 1.1 |
| Threonine | 4.8 | Isoleucine | 4.2 |
| Serine | 4.4 | Leucine | 6.7 |
| Glutamic | 17.1 | Tyrosine | 2.6 |
| Proline | 3.0 | Phenylalanine | 3.8 |
| Glycine | 4.0 | Tryptophan | 1.0 |

| Typical Vitamin Analysis (mg/100gm) | |
|---|---|
| Thiamine | 0.7 |
| Riboflavin | 4.7 |
| Pyridoxine HCl | 1.4 |
| Pantothenic Acid | 10.0 |
| Biotin | 0.03 |
| Niacin | 41 |
| Folic Acid (total) | 0.3 |
| Folic Acid (free) | 0.1 |
| PABA | 0.7 |
| Inositol | 460 |
| Choline Chloride | 525 |
| Vitamin B-12 | 0.0001 |

*Ether-extractable fat is about 0.2%

EXAMPLE 6: Processed Cheese

| INGREDIENTS | PERCENT BY WEIGHT | |
|---|---|---|
| | Test | Control |
| Cheddar cheese, grated | 14.66 | 14.66 |
| Brick cheese, grated | 54.69 | 58.66 |
| American cheese, grated | 14.66 | 14.66 |
| Sodium aluminum phosphate basic | 2.56 | 2.56 |
| Salt | 0.37 | 0.37 |
| Vegetable oil | 1.32 | 0.00 |
| Water | 10.42 | 9.09 |
| Heat-treated yeast | 1.32 | 0.00 |

DIRECTIONS:

1. Combine in steam kettle: ¼ of cheese, ½ of water, stir until slightly melted.
2. Add salt, sodium aluminum phosphate, heat-treated yeast (blend with oil) and remainder of water and cheese.
3. Heat to 71° C.—mold.

BENEFITS:
1. Heightens cheese flavor.
2. Promotes smooth mouthfeel.

EXAMPLE 7: Low Calorie (6% Oil) Creamy Garlic Dressing

| INGREDIENTS | PERCENT BY WEIGHT | |
|---|---|---|
| | Test | Control |
| Water | 62.21 | 61.31 |
| Vinegar, 100 grain | 14.00 | 14.00 |
| Sugar | 12.30 | 12.30 |
| Vegetable oil | 6.00 | 6.00 |
| Salt | 2.20 | 2.00 |
| Egg yolk, 10% salt | 0.00 | 2.00 |
| Heat-treated yeast | 0.90 | 0.00 |
| Gum tragacanth[a] | 0.92 | 0.92 |
| Garlic powder | 0.50 | 0.50 |
| Lemon juice | 0.50 | 0.50 |
| Propylene glycol alginate[b] | 0.35 | 0.35 |
| Potassium sorbate[c] | 0.10 | 0.10 |
| Calcium disodium EDTA[d] | 0.02 | 0.02 |

Directions
1. Combine sugar, gums, and water; blend[e] for 15 minutes on speed 1.
2. Add seasonings, lemon juice, and vinegar, blend for 1 minute on speed 2.
3. Add egg and heat-treated yeast, blend for 2 minutes on speed 2.
4. Slowly add oil while mixing on speed 2.
5. Process through colloid mill.

Benefits
1. Lowers ingredient costs
2. Functionally replaces egg yolk
3. Balances flavor a: T-400, Stein, Hall and Co., New York, N.Y.
b: Kelcoloid HVF, Kelco Co., Chicago, Ill.
c: Sorbistat-K, Pfizer Inc., New York, N.Y.
d: Versene CA, Dow Chemical Co., Midland, Mich.
e: Hobart N-50 Mixer EXAMPLE 8: Thousand Island Dressing

| INGREDIENTS | PERCENT BY WEIGHT | |
|---|---|---|
| | Test | Control |
| Vegetable oil | 36.55 | 36.55 |
| Water | 35.12 | 34.55 |
| Sugar | 8.07 | 8.07 |
| Vinegar, 100 grain | 6.75 | 6.75 |
| Sweet pickle relish | 6.57 | 6.57 |
| Salt | 1.41 | 1.28 |
| Egg yolk, 10% salt | 1.34 | 3.35 |
| Heat-treated yeast | 1.31 | 0.00 |
| Gum tragacanth[a] | 1.31 | 1.31 |
| Lemon juice | 0.45 | 0.45 |
| Propylene glycol alginate[b] | 0.40 | 0.40 |
| Mustard, dry | 0.33 | 0.33 |
| Garlic powder | 0.16 | 0.16 |
| Onion powder | 0.16 | 0.16 |
| Paprika | 0.04 | 0.04 |
| Calcium disodium EDTA[c] | 0.03 | 0.03 |

DIRECTIONS
1. Combine sugar and gum; add to water blend[d] for 15 minutes on speed 1.
2. Add seasonings, vinegar, and lemon juice; mix for 1 minute on speed 2.
3. Add egg and heat-treated yeast; mix for 1 minute on speed 2.
4. Add oil slowly at first, blend well on speed 2.
5. Process twice through colloid mill.
6. Add sweet pickle relish.

BENEFITS
1. Functionally replaces egg yolk.
2. Lowers ingredient costs.

a: T-400, Stein, Hall and Company, N.Y., N.Y.
b: Kelcoloid HVG, Kelco Company, Chicago, Illinois
c: Versene CA, Dow Chemical Company, Midland, Mich.
d: Hobart N-50 mixer EXAMPLE 9: Creamy French Dressing

| INGREDIENTS | PERCENT BY WEIGHT | |
|---|---|---|
| | Test | Control |
| Vegetable Oil | 39.00 | 39.00 |
| Water | 37.47 | 36.86 |
| Sugar | 8.61 | 8.61 |
| Vinegar, 100 grain | 7.20 | 7.20 |
| Salt | 1.50 | 1.36 |
| Egg yolk, 10% salt | 1.43 | 3.58 |
| Heat-treated yeast | 1.40 | 0.00 |
| Gum tragacanth[a] | 1.40 | 1.40 |
| Lemon juice | 0.48 | 0.48 |
| Propylene glycol alginate[b] | 0.42 | 0.42 |
| Mustard, dry | 0.36 | 0.36 |
| Paprika | 0.36 | 0.36 |
| Garlic powder | 0.17 | 0.17 |
| Onion powder | 0.17 | 0.17 |
| Calcium disodium EDTA[c] | 0.03 | 0.03 |

DIRECTIONS
1. Combine sugar and gum; add to water blend[d] for 15 minutes on speed 1.
2. Add seasonings, vinegar, and lemon juice; mix for 1 minute on speed 2.
3. Add egg and heat-treated yeast; mix for 1 minute on speed 2.
4. Add oil, slowly at first, blend well on speed 2.
5. Process twice through colloid mill.

BENEFITS
1. Heightens spice flavor.
2. Lowers ingredient costs.

a: T-400 Stein, Hall and Company, N.Y., N.Y.
b: Kelcoloid HVF, Kelco Company, Chicago, Ill.
c: Versene CA, Dow Chemical Company, Midland, Mich.
d: Hobart N-50 Mixer EXAMPLE 10: Onion and Chives Dressing

| INGREDIENTS | PERCENT BY WEIGHT | |
|---|---|---|
| | Test | Control |
| Vegetable oil | 37.46 | 37.46 |
| Water | 36.02 | 35.40 |
| Sugar | 8.27 | 8.27 |
| Vinegar, 100 grain | 6.92 | 6.92 |
| Egg albumen, dry | 3.36 | 3.36 |
| Salt | 1.44 | 1.30 |
| Egg yolk, 10% salt | 1.40 | 3.50 |
| Heat-treated yeast | 1.34 | 0.00 |
| Gum tragacanth[a] | 1.34 | 1.34 |
| Lemon juice | 0.46 | 0.46 |
| Propylene glycol alginate[b] | 0.40 | 0.40 |
| Chives, dried, chopped | 0.40 | 0.40 |
| Onions, instant minced | 0.40 | 0.40 |
| Mustard, dry | 0.34 | 0.34 |
| Garlic powder | 0.17 | 0.17 |
| Onion powder | 0.17 | 0.17 |
| Paprika | 0.04 | 0.04 |
| Turmeric | 0.04 | 0.04 |

|  | PERCENT BY WEIGHT | |
|---|---|---|
| INGREDIENTS | Test | Control |
| Calcium disodium EDTA[c] | 0.03 | 0.03 |

DIRECTIONS

1. Combine sugar and gum; add to water, blend for 15 minutes on speed 1.
2. Add seasonings, vinegar, and lemon juice; mix for 1 minute on speed 2.
3. Add egg and heat-treated yeast; mix for 1 minute on speed 2.
4. Add oil slowly at first, blend well on speed 2.
5. Process twice through colloid mill.
6. Add onions and chives.

BENEFITS

1. Functionally replaces egg yolk.
2. Enhances onion flavor.
3. Lowers ingredient costs.

a: T-400, Stein, Hall and Company, N.Y., N.Y.
b: Kelcoloid HVF, Kelco Company, Chicago, Ill.
c: Versene CA, Dow Chemical Company, Midland, Mich.
d: Hobart N-50 Mixer

EXAMPLE 11: Novel Sour Cream Flavored Dressing

|  | PERCENT BY WEIGHT | |
|---|---|---|
| INGREDIENTS | Test | Control |
| Vegetable oil | 37.78 | 37.78 |
| Water | 36.30 | 35.74 |
| Sugar | 8.34 | 8.34 |
| Vinegar, 100 grain | 6.96 | 6.96 |
| Egg albumen | 3.40 | 3.40 |
| Salt | 1.45 | 1.30 |
| Egg yolk, 10% salt | 1.38 | 3.45 |
| Heat-treated yeast | 1.36 | 0.00 |
| Gum tragacanth[a] | 1.36 | 1.36 |
| Lemon juice | 0.47 | 0.47 |
| Propylene glycol alginate[b] | 0.40 | 0.40 |
| Mustard dry | 0.35 | 0.35 |
| Garlic powder | 0.17 | 0.17 |
| Onion powder | 0.17 | 0.17 |
| Paprika | 0.04 | 0.04 |
| Turmeric | 0.04 | 0.04 |
| Calcium disodium EDTA[c] | 0.03 | 0.03 |

DIRECTIONS

1. Combine sugar and gum; add to water blend[d] for 15 minutes on speed 1.
2. Add seasonings, vinegar, and lemon juice; mix for 1 minute on speed 2.
3. Add egg and heated-treated yeast; mix for 1 minute on speed 2.
4. Add oil slowly at first, blend well on speed 2.
5. Process twice through colloid mill.

BENEFITS

1. Functionally replaces egg yolk.
2. Thickens dressing.
3. Lowers ingredient costs.

a: T-400 Stein, Hall and Company, N.Y., N.Y.
b: Kelcoloid HVF, Kelco Company, Chicago, Ill.
c: Versene CA, Dow Chemical Company, Midland, Mich.
d: Hobart N-50 Mixer

EXAMPLE 12: Low Calorie (12% Oil) Creamy Garlic Dressing

|  | PERCENT BY WEIGHT | |
|---|---|---|
| INGREDIENTS | Test | Control |
| Water | 53.96 | 53.50 |
| Vinegar, 50 grain | 15.55 | 15.55 |
| Sugar | 12.30 | 12.30 |
| Vegetable oil | 12.00 | 12.00 |
| Salt | 2.50 | 2.39 |
| Egg yolk, 10% salt | 1.02 | 2.04 |
| Heat-treated yeast | 0.45 | 0.00 |
| Gum tragacanth[a] | 0.75 | 0.75 |
| Garlic powder | 0.50 | 0.50 |
| Lemon juice | 0.50 | 0.50 |
| Propylene glycol alginate[b] | 0.35 | 0.35 |
| Potassium sorbate[c] | 0.10 | 0.10 |
| Calcium disodium EDTA[d] | 0.02 | 0.02 |

DIRECTIONS

1. Combine sugar and gum; add to water blend[e] for 15 minutes on speed 1.
2. Add seasonings, vinegar, and lemon juice; mix for 1 minute on speed 2.
3. Add egg and heat-treated yeast; mix for 1 minute on speed 2.
4. Add oil, slowly at first, blend well on speed 2.
5. Process twice through colloid mill.

BENEFITS

1. Lowers ingredient costs
2. Functionally replaces egg yolk
3. Balances flavor a: T-400, Stein, Hall and Co., N.Y., N.Y.
b: Kelcoloid HVF, Kelco Company, Chicago, Ill.
c: Sorbistat-K, Pfizer, Inc., N.Y., N.Y.
d: Versene CA, Dow Chemical Company, Midland, Mich.
e: Hobart N-50 Mixer

EXAMPLE 13: Chili Mac

|  | PERCENT BY WEIGHT | |
|---|---|---|
| INGREDIENTS | Test | Control |
| Beef chuck | 27.28 | 27.86 |
| Beef navels | 10.91 | 11.14 |
| Cooked macaroni | 29.11 | 29.71 |
| Tomato paste | 9.10 | 9.29 |
| All purpose flour | 1.82 | 1.86 |
| Seasoning mix* | 1.21 | 1.95 |
| Salt | 1.10 | 1.11 |
| Brown sugar | .36 | .37 |
| Water | 17.07 | 16.71 |
| Heat-treated yeast | 2.04 | — |

| Seasoning Mix | Percent by Weight |
|---|---|
| Onion powder | 1.02 |
| Chili powder | 59.90 |
| Spanish paprika | 20.30 |
| Ground cumin | 12.18 |
| Garlic powder | 2.03 |
| Black pepper | 1.02 |
| Ground oregano | 3.05 |
| Cayanne pepper | .50 |

Directions

1. Precook macaroni in water containing 2% salt. Boil for at least 12 minutes. Wash and rinse pasta in cold water and drain.
2. Grind all the beef through a ⅜" plate.
3. Blend the flour, salt, seasoning, heat-treated yeast and tomato paste with approximately ½ the water until a smooth paste is attained. Add the ground beef and remaining water and blend.
4. Add the cooked macaroni mix and can.

Benefits

1. Heightens chili flavor.
2. Reduces free surface fat after retorting.

3. Reduces spice use by 38 percent.

EXAMPLE 14: Sour Cream Flavored Sauce

| INGREDIENTS | PERCENT BY WEIGHT | |
|---|---|---|
| | Test | Control |
| Sour cream solids | 15.00 | 20.00 |
| Nonfat dry milk | 20.00 | 20.00 |
| Hydrogenated vegetable shortening | 15.00 | 15.00 |
| Butter milk solids | 10.00 | 15.00 |
| Whey, dried powder | 10.00 | 10.00 |
| Sodium alginate | 5.00 | 5.00 |
| Citric acid | 4.00 | 4.00 |
| Salt | 4.00 | 4.00 |
| Monosodium glutamate | — | 3.00 |
| Onion powder | 3.00 | 3.00 |
| Tetrasodium pyrophosphate | 0.5 | 0.5 |
| Dried chives, chopped | 0.5 | 0.5 |
| Heat-treated yeast | 13.0 | — |

DIRECTIONS
1. Dry blend all the ingredients.
2. Package in 1.5 ounce packages.
3. Blend contents of one package with ½ cup of cold milk, allow mixture to stand for 15 minutes, mix and serve.

BENEFITS
1. Heightens sour cream flavor.
2. Replaces monosodium glutamate.
3. Partially replaces buttermilk solids.
4. Increases smooth mouthfeel.
5. Lowers ingredient cost.
6. Partially replaces sour cream solids.

EXAMPLE 15: Taco Seasoning

| INGREDIENTS | PERCENT BY WEIGHT | |
|---|---|---|
| | Test | Control |
| Onion powder | 12.00 | 15.00 |
| Dried whey | 15.00 | 15.00 |
| Salt | 15.00 | 15.00 |
| Chili pepper | 10.00 | 15.00 |
| Monosodium glutamate | 5.00 | 10.00 |
| Cumin | 5.00 | 5.00 |
| Paprika | 5.00 | 5.00 |
| Garlic powder | 4.00 | 5.00 |
| Potato starch | 4.00 | 4.00 |
| Oregano | 4.00 | 4.00 |
| Tomato powder | 4.00 | 4.00 |
| Citric acid | 3.00 | 3.00 |
| Heat-treated yeast | 14.00 | — |

DIRECTIONS
1. Dry blend all the ingredients.
2. Package in 1.5 ounce package.
3. Recommend browning 1 lb. of ground lean beef, adding ¾ cup of water and the seasoning package ingredients. Bring this product to a boil and simmer.

BENEFITS
1. Heightens chili flavor.
2. Partially replaces monosodium glutamate.
3. Partially replaces garlic powder.
4. Partially replaces onion powder.
5. Lowers ingredient cost.

EXAMPLE 16: Sponge Cake

| INGREDIENTS | PERCENT BY FLOUR WEIGHT | |
|---|---|---|
| | Test | Control |
| Cake flour | 100.00 | 100.00 |
| Granulated sugar | 120.00 | 120.00 |
| Water | 123.00 | 120.00 |
| Egg, yolk, fresh | 6.00 | 12.00 |
| Heat-treated yeast | 3.00 | 0.00 |
| Nonfat dry milk | 7.50 | 7.50 |
| Egg, white, fresh | 7.00 | 7.00 |
| Emulsifier* | 5.00 | 5.00 |
| Salt | 3.00 | 3.00 |
| Baking powder | 2.75 | 2.75 |
| Flavor** | 2.00 | 2.00 |

DIRECTIONS:
1. Mix all dry ingredients and emulsifier until homogeneous.
2. Add 3/5 of the water (ice water) and flavor, mix,*** scrape bowl after each mixing period as follows: ½ minute on speed 1, 1 minute on speed 2, 3 minutes on speed 3, and 3 minutes on speed 4.
3. Add balance of water and mix, scrape bowl after each mixing period as follows: ½ minute on speed 1, 2 minutes on speed 2, 4 minutes on speed 1, and 2 minutes on speed 2.
4. Specific gravity should be 0.510–0.525; if not, mix an additional 30 seconds on speed 3.
5. Scale 10 oz. in 6½" ungreased tube pan or 8" round pan.
6. Bake at 375° F. for 25–30 minutes.

*Atmos 2462, ICI America Inc., Wilmington, DE Vanilla extract, B. A. Railton Co., Northlake, IL *Hobart A-100

Benefits:
1. Partially replaces egg yolk.
2. Improves bite quality—stronger bite quality.
3. Lowers ingredient cost.

These examples are only illustrative of some of the many applications to which the heat-treated single-cell materials of this invention are suited. It will be obvious to those skilled in the art that many variations from these examples, shown for purposes of illustration, can be made without departing from the scope of this invention.

We claim:

1. A process for treating whole single-cell protein cells consisting essentially of heating an aqueous slurry of the cells to a temperature of from about 215° to about 300° F. for a period of time of from about 30 seconds to about 25 minutes to deactivate invertase whereby heat treated whole cells are obtained having improved functional properties.

2. The process of claim 1 wherein the temperature range is from about 255° to about 300° F.

3. The process of claim 1 wherein the temperature range is from about 260° to about 270° F.

4. The process of claim 3 wherein the single-cell protein is a yeast.

5. The process of claim 4 wherein the yeast is selected from the group consisting of *Candida utilis*, *Saccharomyces cerevisiae*, *Saccharomyces fragilis*, and *Saccharomyces carlsbergensis*.

6. The process of claim 4 wherein the yeast is *Candida utilis*.

7. In a process for producing a food-quality yeast wherein a yeast broth is withdrawn from a fermentation zone, said yeast broth being subsequently concentrated to a cream which is subsequently spray-dried to a powder form, the improvement consisting essentially of heating the yeast cream to a temperature of from about 215° to about 300° F. for from about 30 seconds to about 25 minutes to deactivate invertase whereby a heat treated cell cream is obtained having improved functional properties.

8. The process of claim 7 wherein the temperature is from about 255° to about 275° F.

9. The process of claim 7 wherein the temperature is from about 260° to about 270° F.

10. A process for treating an aqueous slurry of whole single-cell protein cells consisting essentially of heating the slurry at a temperature of from about 255° to about 275° F. for a period of time sufficient to deactivate invertase whereby heat treated whole cells are obtained having improved functional properties.

11. The process of claim 10 wherein the slurry is heated to a temperature of about 255° F. for at least 5 minutes.

12. The process of claim 10 wherein the slurry is heated to a temperature of about 260° F. for about 2 minutes.

13. The process of claim 10 wherein the slurry is heated to a temperature of about 270° F. for about 2 minutes.

14. The process of claim 10 wherein the single-cell protein is a yeast.

15. The process of claim 14 wherein the yeast is selected from the group consisting of *Candida utilis, Saccharomyces cerevisiae, Saccharomyces fragilis,* and *Saccharomyces carlsbergensis.*

16. The process of claim 14 wherein the yeast is *Candida utilis.*

17. The process of claim 14 wherein the yeast is active.

18. The process of claim 14 wherein the yeast is inactive.

19. The product of the process of claim 10.

20. In a process for producing a food-quality yeast wherein a yeast broth is withdrawn from a fermentation zone, said yeast broth being subsequently concentrated to a cream which is subsequently spray-dried to a powder form, the improvement consisting essentially of heating the yeast cream to a temperature of from about 255° to about 275° F. for a period of time about sufficient to deactivate invertase whereby a heat treated yeast cream is obtained having improved functional properties.

21. The process of claim 20 wherein the yeast cream is heated to a temperature of about 265° F.

22. The process of claim 21 wherein the yeast cream is held at about 265° F. for from about 2 to about 2.5 minutes.

23. In a process for the continuous production of food quality yeasts by aerobic growth of said yeasts in a fermentation zone on an aqueous ethanolic substrate in the presence of ammonia, an oxygen-containing gas, and an excess of essential nutrients, wherein said yeasts are withdrawn from said fermentation zone as a broth, concentrated to a cream by centrifugation, and spray-dried to powder form, the improvement consisting essentially of heating the yeast cream to a temperature of from about 260° to about 270° F. for a length of time of from about 2 to about 2.5 minutes to inactivate invertase whereby a heat treated yeast cream is obtained having improved functional properties.

24. The process of claim 23 wherein the yeast is *Candida utilis.*

25. The process of claim 24 wherein the yeast cream is heated to about 265° F. for from about 2 to about 2.5 minutes.

26. The product of the process of claim 23.